US00PP28606P3

(12) United States Plant Patent
Jacobs

(10) Patent No.: US PP28,606 P3
(45) Date of Patent: Nov. 7, 2017

(54) ***CHRYSANTHEMUM* PLANT NAMED 'ZANMUSKYFA WHITE'**

(50) Latin Name: ***Chrysanthemum×morifolium* Ramat.**
Varietal Denomination: Zanmuskyfa White

(71) Applicant: Chrysanthemum Breeders Association Research B.V., Valkenburg ZH (NL)

(72) Inventor: Henricus Cornelius Maria Jacobs, Valkenburg (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 91 days.

(21) Appl. No.: 14/757,489

(22) Filed: Dec. 23, 2015

(65) Prior Publication Data
US 2017/0188499 P1 Jun. 29, 2017

(51) Int. Cl.
*A01H 5/02* (2006.01)

(52) U.S. Cl.
USPC ..... Plt./288

(58) Field of Classification Search
USPC ..... Plt./288
See application file for complete search history.

*Primary Examiner* — Anne Grunberg
(74) *Attorney, Agent, or Firm* — Steptoe & Johnson LLP

(57) ABSTRACT

A *chrysanthemum* plant named 'Zanmuskyfa White' characterized by its small sized blooms with white ray floret and a cream center, and prolific branching; natural season flower date October 19 (week 43); blooming for a period of 5 weeks.

3 Drawing Sheets

Botanical designation: *Chrysanthemum×morifolium* Ramat.

Cultivar denomination: "Zanmuskyfa White".

RELATED CULTIVARS

The new plant is a flower color mutant of 'Zanmuskyfa Purple'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmuskyfa White'. 'Zanmuskyfa White' is a product of a breeding and selection program which had the objective of finding flower color mutants from existing parent plants. The new plant comprises a whole plant mutant of the parent *chrysanthemum* named 'Zanmuskyfa Purple' (unpatented). Plants from the new cultivar 'Zanmuskyfa White' differ from plants of the female parent in the color of the ray-florets. The ray-florets of the parent are purple, while those of the new plant are white.

In order to obtain color mutants, unrooted cuttings of the parent plant were irradiated in April 2013 at Ziekenhuis, Rotterdam, the Netherlands, with gamma radiation at a dose of 15 Gy. These treated cuttings were then planted in a controlled environment (greenhouse) in Rijsenhout, the Netherlands. In this population of planted cuttings an individual plant was found by Henricus Cornelis Maria Jacobs in May 2013 which had white inflorescences. This flower color mutant was subsequently selected for further tests in the same controlled environment in Rijsenhout, the Netherlands. The first act of asexual reproduction of 'Zanmuskyfa White' was accomplished when after planting of the selected plant as a motherplant in July 2013, vegetative cuttings from this motherplant were taken and propagated further in Rijsenhout, the Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *chrysanthemum* (of about 22 weeks) is shown in the accompanying drawings, the color being as nearly true as possible with color photographs of this type.

DESCRIPTION OF THE INVENTION

Figure 1:
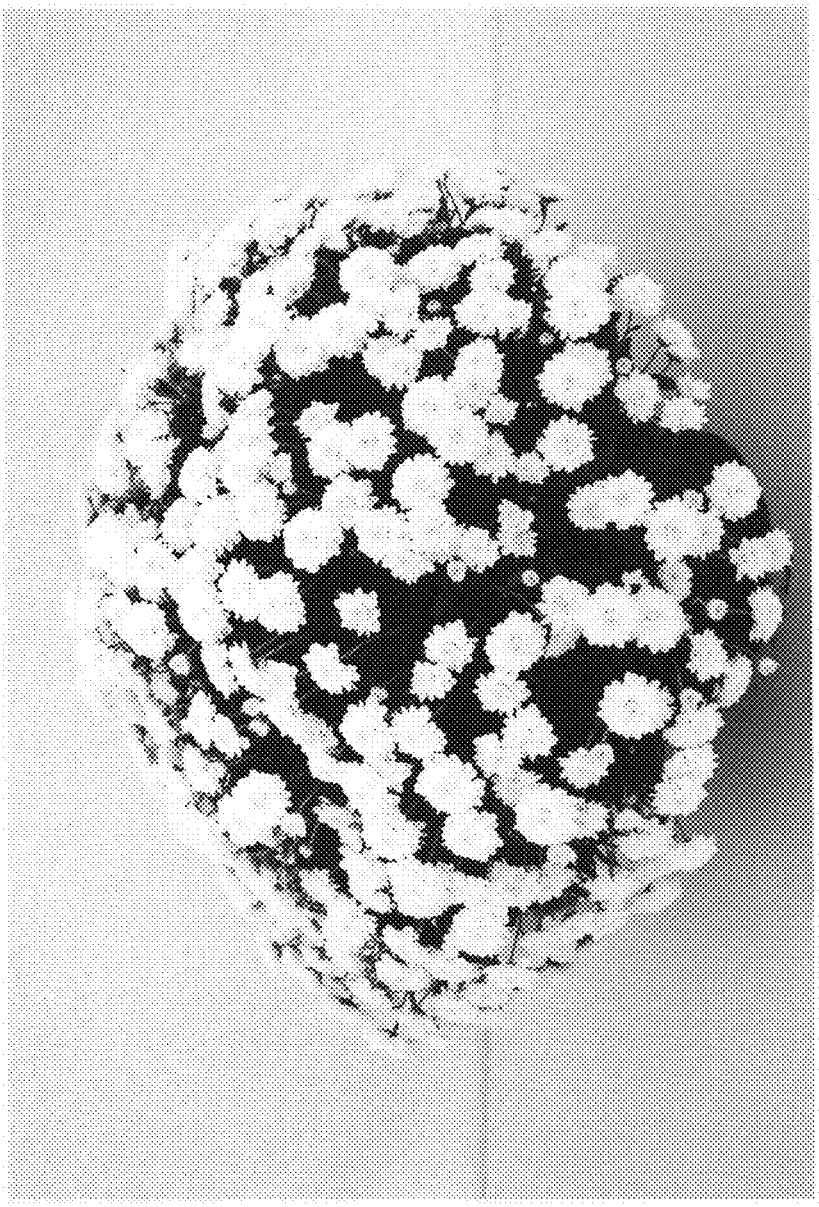
FIG. 1 shows a plant of the cultivar in full bloom.
Figure 2:
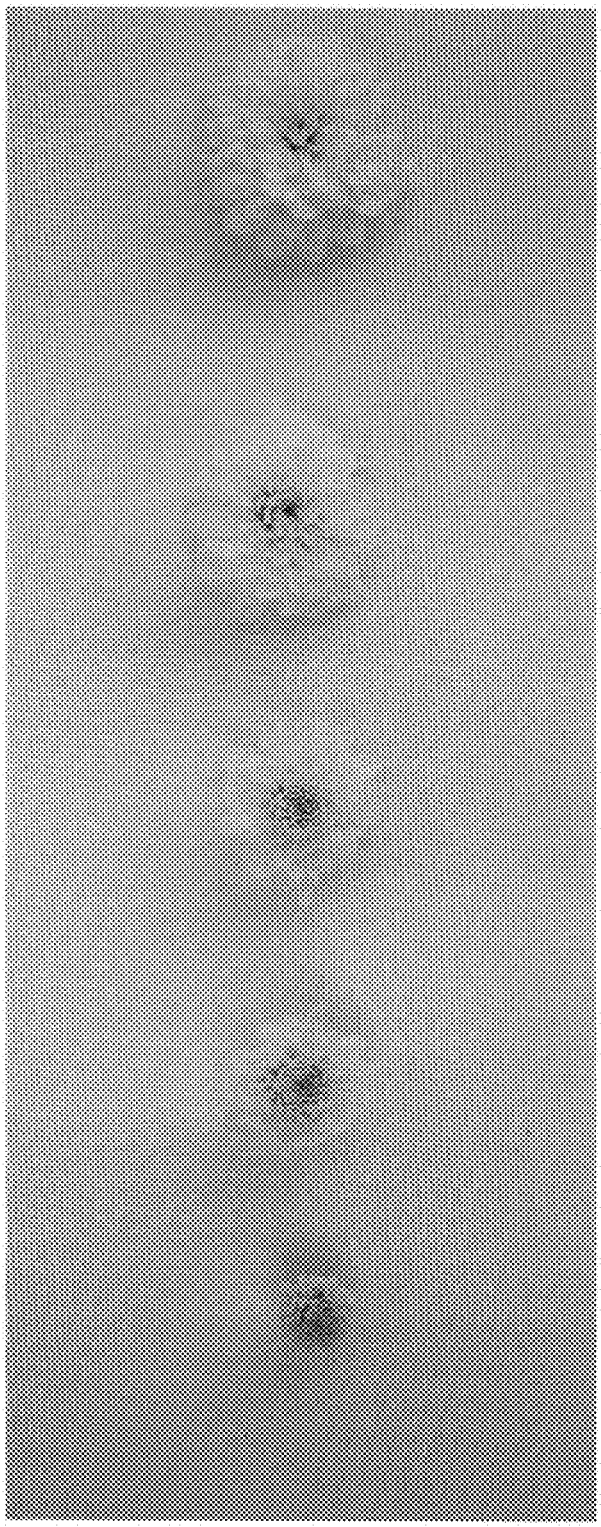
FIG. 2 shows the various stages of blooms of the new cultivar.
Figure 3:
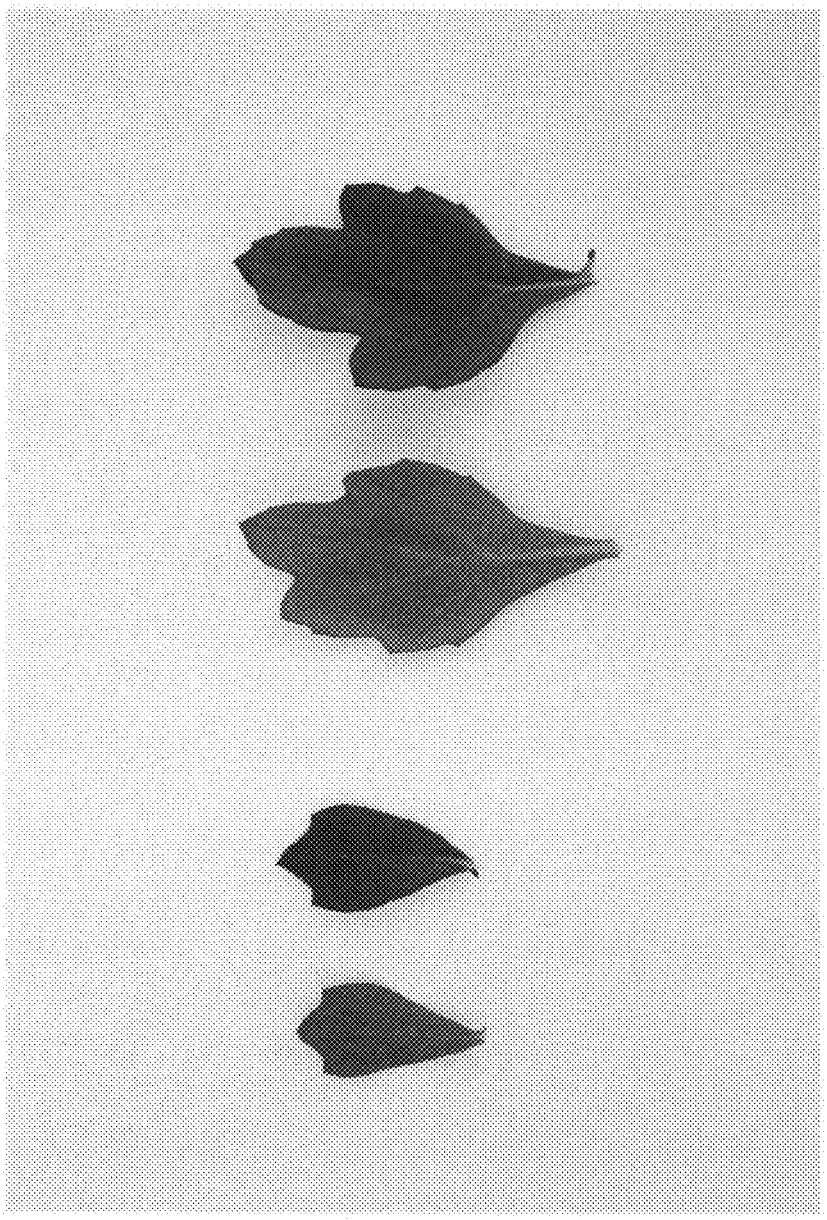
FIG. 3 shows the various stages of foliage of the new cultivar.

The observations and measurements were gathered from plants in the period of 21 to 25 weeks of age grown outdoor in Rijsenhout, the Netherlands, under natural day length and temperature and planted in week 23 in 2015. The natural blooming date of this crop was October 19 (week 43). The average height of the plants was 25 cm. No growth retardants were used. No tests were done on disease or insects resistance or susceptibility. No tests were done on cold or drought resistance. This new variety produces small sized blooms with white ray florets and a cream center blooming for a period of four weeks.

From the cultivars known to the inventor the most similar existing cultivar in comparison to 'Zanmuskyfa White' is its parent 'Zanmuskyfa Purple' (unpatented). When 'Zanmuskyfa Purple' and 'Zanmuskyfa White' are being compared the following difference is noticed: 'Zanmuskyfa Purple' has purple blooms, while 'Zanmuskyfa White' has white blooms.

The following is a description of the plant and characteristics that distinguish "Zanmuskyfa White" as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* × *morifolium* Ramat. 'Zanmuskyfa White'

| | |
|---|---|
| **Bud** | |
| Size: | Small; cross-section 4 mm, height 2 mm |
| Shape: | Round |
| Texture: | Pubescent |
| Outside color: | Greyed-green 191A |
| **Phyllaries** | |
| Number: | 18-21., arranged in 3 rows |
| Shape: | Elliptic |
| Apex: | Acute |
| Base: | Truncate |
| Margin: | Entire |
| Color: | Upper side: Greyed-green 191A<br>Lower side: Green 143A |
| Length and width: | 3-4 mm; 1.5 mm |
| Texture: | Pubescent |
| **Inflorescences** | |
| Type: | Double |
| Height: | 0.8 cm |
| Diameter: | 3 cm |
| Peduncle length: | 5-5.5 cm |
| Peduncle color: | Green 138B |
| Peduncle diameter: | 1.5 nun |
| Peduncle texture: | Pubescent |
| Peduncle strength: | Weak |
| Number per branch; | About 5-6 inflorescences |
| Duration of flowering: | 5 weeks |
| Seed set: | Has not been determined to date |
| Fragrance: | Faint chrysanthemum odor |
| **Color inflorescences** | |
| Center of inflorescence: | White 155A |
| Color of upper side of ray florets: | Outer rows: White N155D;<br>Inner rows: White 155A |
| Color of lower side of ray florets: | Outer rows: White N155D;<br>Inner rows: While 155A |
| Tonality from distance: | A garden mum with white blooms and a cream center |
| Color of ray florets after aging of the plant: | White 155A |
| **Ray florets** | |
| Number of types: | One |
| Type: | Ligulate |
| Texture: | Upper and lower side smooth |
| Number: | 140-150 |
| Shape: | Narrowly elliptic to Elliptic |
| Apex: | Pointed |
| Base: | Acute |
| Cross-section: | Flat |
| Longitudinal axis: | Straight |
| Length of corolla tube: | 2 mm |
| Diameter corolla tube: | 1 mm |
| Ray floret margin: | Entire |
| Ray floret length: | 0.6-1.2 cm |

TABLE 1-continued

Botanical Description of *Chrysanthemum* × *morifolium* Ramat. 'Zanmuskyfa White'

| | |
|---|---|
| Ray-floret width: | 2-5 mm |
| Disc florets | Absent |
| **Receptacle** | |
| Color: | Yellow-green 145D |
| Shape: | Domed raised |
| Height | 2 mm |
| Diameter: | 2 mm |
| **Reproductive Organs** | |
| Androecium: | Absent |
| Pollen: | Absent |
| Gynoecium: | Present on ray florets |
| Style color: | Yellow-green 154C |
| Style length: | 4 mm |
| Stigma color: | Yellow 7A |
| Stigma width: | 1 mm |
| Ovary: | Enclosed in calyx |
| Ovary color: | Yellow-green 149D |
| **Plant** | |
| Type: | Bushy |
| Growth habit: | Spherical shape |
| Growth rate: | Medium |
| Height: | 20-25 cm |
| Width: | 45 cm |
| Stem color: | Greyed-brown 199A |
| Stem strength: | Weak |
| Stem brittleness: | Brittle |
| Stem anthocyanin coloration: | absent |
| Internode length: | 0.8-2.5 cm |
| Length of lateral branch: | From top to bottom 14-15 cm |
| Lateral branch color: | Green 138C |
| Lateral branch, attachment: | Weak |
| Lateral branch diameter: | 2 .mm |
| Lateral branch texture: | Rough with ribs |
| Branching (average number of lateral branches): | Dense- with 10 to 12 breaks after pinching |
| Natural season blooming date: | October 19 (week 43) in Rijsenhout, the Netherlands. |
| Root habits: | Fine, freely branching |
| Root color: | White 155D; 6-8 days, formation |
| Rooting time: | rooted plants: 12-14 days |
| **Foliage** | |
| Leaf glossines: | Upper side: weak; Lower side: absent |
| Leaf color: | Upper side: Yellow-green 147A;<br>Lower side: Green 138A |
| Color midvein: | Upper side: Yellow-green 147D;<br>Lower side: Yellow-green 148D |
| Size: | Small; length 3-4.5 cm, width 1.8-2.5 cm |
| Quantity (number per lateral branches): | 14-15 |
| Shape: | Elliptic |
| Texture upper side: | Sparsely pubescent |
| Texture under side: | Pubescent |
| Venation arrangement: | Pinnate |
| Shape of margin: | Serrated |
| Shape of base of sinus between lateral lobes: | Rounded |
| Margin of sinus between lateral lobes: | Diverging |
| Shape of base: | Acute to truncate |

TABLE 1-continued

| Botanical Description of *Chrysanthemum* × *morifolium* Ramat. 'Zanmuskyfa White' | |
|---|---|
| Apex: | Mucronulate |
| Petiole altitude: | Strongly upwards |
| Petiole length: | 0.5-0.8 cm |
| Petiole diameter: | 15 mm |
| Petiole color: | Yellow-green 147D |
| Stipule: | very small, about 0.5 mm |

TABLE 2

| Differences with the comparison variety, when grown under identical conditions | | |
|---|---|---|
| | "Zanmuskyfa White" | 'Zanmuskyfa Purple' |
| Color ray-florets | white | purple |

I claim:

1. A new and distinct *chrysanthemum* plant named 'Zanmuskyfa White' as described and illustrated.

* * * * *